United States Patent [19]
Schonberger

[11] Patent Number: 6,077,228
[45] Date of Patent: Jun. 20, 2000

[54] BREAST TEMPERATURE SCANNER

[76] Inventor: Milton Schonberger, 1005 Ash Dr., Mahwah, N.J. 07430

[21] Appl. No.: 09/186,500

[22] Filed: Nov. 4, 1998

[51] Int. Cl.⁷ ....................................................... A61B 5/00
[52] U.S. Cl. ............................ 600/549; 600/555; 374/45; 374/100
[58] Field of Search .................................. 600/549, 555; 374/15, 45, 100, 112, 137

[56] References Cited

U.S. PATENT DOCUMENTS

| | | | |
|---|---|---|---|
| 3,830,224 | 8/1974 | Vanzetti et al. | 600/549 |
| 3,960,138 | 6/1976 | Doss et al. | 600/549 |
| 3,970,074 | 7/1976 | Mogos et al. | 128/2 |
| 4,055,166 | 10/1977 | Simpson et al. | 600/549 |
| 4,445,516 | 5/1984 | Wollnik et al. | 128/736 |
| 4,524,778 | 6/1985 | Brown, Jr. et al. | 600/549 |
| 4,624,264 | 11/1986 | Sagi | 600/549 |
| 4,955,380 | 9/1990 | Edell | 600/355 |
| 5,255,979 | 10/1993 | Ferrari | 600/549 |
| 5,301,681 | 4/1994 | DeBan et al. | 600/549 |
| 5,810,010 | 9/1998 | Anbar | 128/664 |
| 5,830,159 | 11/1998 | Netta | 600/549 |

*Primary Examiner*—Cary O'Connor
*Assistant Examiner*—Charles Marmor, II
*Attorney, Agent, or Firm*—Ostrolenk, Faber, Gerb & Soffen, LLP

[57] ABSTRACT

An arrangement and a method for scanning the human breast for localized areas of elevated temperature and which areas do not cool as rapidly as other areas. An array of closely spaced apart, small mass thermistors is supported on several, circle segment, flexible substrate support panels that are adhered to the skin for producing concentric circular closely spaced arrays of thermistors, each connected to a pair of conductors on the panels. The conductors are connected through a connector to a circuit which measures the voltage and/or resistance of each of the thermistors, which is dependent upon its temperature. The voltage and/or resistance and thereby the temperature of each thermistor is measured at several second intervals. A test subject is iced for causing vasoconstriction, and the rate of temperature change in each of the thermistors is noted, to note which localized area of the breast does not cool as rapidly as other areas, or to show other cooling profiles.

20 Claims, 2 Drawing Sheets

BREAST TEMPERATURE SCANNER

BACKGROUND OF THE INVENTION

The present invention relates to an apparatus and a method for determining localized temperatures in the breast and for detecting and assessing changes in temperature of localized areas, which is particularly useful in screening for possible localized malignancies within the breast.

Screening for breast cancer is an important diagnostic procedure. The cure rate for breast cancer before metastases are present is quite high. Hence, early detection of malignancies using a non-damaging technique is desirable.

In the United States, x-ray mammography of the breast is a primary diagnostic procedure. Patients are reluctant to be exposed to x-rays. Physicians are reluctant to prescribe mammograms, especially for women under 40 years of age. Further, younger women often have too dense tissue which makes radiographic interpretation difficult. Another factor that enters into the decisions about using mammography is the costs of the equipment required, the facility for the equipment, the x-ray technician and the diagnostician required after the test is performed. Further, x-ray mammography often is only able to detect tumors after they have been in existence for a long time, and this can present a problem with cancer detection. For example, x-ray mammography relies for the most part on microcalcification which results when the tumor has grown enough to outstrip its blood supply and parts of the tumor die, turn necrotic and the cell walls are replaced with deposits of calcium which appear as shadows on x-rays. The tumor has likely been in existence for quite some time at this point. Also, mammography can miss at least 10 per cent of all breast cancers, particularly ductal carcinoma in situ.

Yet another technique often used is palpation, which discovers the lump of a tumor by feeling it, but often only discovers the tumor after it has grown for several years.

Several techniques involve taking temperature measurements of the breast, preferably over localized areas of the breast to locate a possible tumor inside the breast. They all rely on the natural process of angiogenesis.

Tumors naturally develop a blood supply to sustain them as they grow. In the 1960's the relationship between angiogenesis and tumor growth was recognized. Angiogenesis is a prognostic indicator for malignancies in the breast. A benign tumor or growth will not develop its own blood supply and will not experience angiogenesis, while a malignant tumor does. There is a detectable differential temperature increase in the region of the tumor, sometimes as much as more than 2° F. As a result of the angiogenesis, heat from the tumor is transmitted to the skin and is measurable at the skin temperature.

When a person is thermally stressed and in particular, the body is chilled, the peripheral blood vessels, including the blood vessels in the breast, constrict, restricting blood flow, which cools the breast tissue. A tumor that has experienced angiogenesis acts as a heat sink, and reacts more slowly, if at all, to thermal stress. The slower reaction of the malignant area as compared with adjacent tissue and other tissue in the breast is an indicator that angiogenesis has occurred and helps locate an area for further examination for presence of a malignant tumor.

One technique of temperature measurement that has been used is infra-red thermography as in a GST test system formerly used. It is effective to detect both benign and malignant tumors that are quite small. An infra-red probe is used to measure the breast temperature. If any area measured has an elevated temperature, the patient's body temperature is chilled to cause vasoconstriction. Temperature measurements are again recorded and compared. Because of angiogenesis, the malignant tissue will not change temperature in the same manner due to the thermal stress, that is, its temperature will only drop a small amount, if at all, as compared with the temperature of normal tissue or the temperature of a benign growth.

A GST test was not accurate enough because of the infra-red probe used and the manner in which the test was administered, so that it had too wide a temperature excursion factor. The device for performing it was too expensive and the analysis process too expensive.

Use of thermographic analysis for locating breast cancer is disclosed, for example in U.S. Pat. Nos. 3,970,074 and 4,445,516.

It has also been proposed to produce an image of breast surface temperature by the use of contacting liquid crystals which provide an image. But the image they supply is very rough or of poor quality. The accuracy of breast temperature measurements by the two known temperature sensing techniques described is not accurate to a precise range. The images obtained by these test procedures are poor in quality generally.

The GST scan, a liquid crystal technique and other temperature sensing techniques, as well as the present invention, rely upon the natural process of angiogenesis.

U.S. Pat. No. 3,970,074 describes an array of thermistors mounted on a resilient sponge that is pressed against the body, whereby the use of thermistors for thermographic detection is known. This arrangement suggests using a plurality of thermistors, but does not describe an optimal arrangement or array of thermistors for breast cancer detection nor an optimal method for using the apparatus for breast cancer detection.

SUMMARY OF THE INVENTION

It is an object of the present invention to provide a non-invasive, non-radiation applying, accurate, relatively inexpensive, easily repeated, simple to use apparatus and technique for locating localized areas within the breast that are abnormally heated and/or do not change temperature at the same rate as other tissue.

Another object is to help detect malignancies or non-malignant growths in the breast.

The present invention utilizes an array of temperature responsive thermistors, each having a voltage and/or resistance that is related to the temperature of the thermistor. The thermistors are supported on a substrate. Each thermistor is connected to conductors leading to a device which measures the voltage and/or resistance of each thermistor and which can also express the temperature of the thermistor as a function of the voltage or resistance. The support with the array of thermistors encircles the breast or at least a large area of the breast. The thermistor array substrate comprises one or more flexible panels, temporarily attachable to the breast. After an initial temperature reading, the patient is thermally stressed, and particularly chilled, to cause vasoconstriction in the breast. Several temperature measurements are made over the thermistor array to determine the change and the rate of change in the temperature at the localized areas of the breast covered by a thermistor. An initially heated area and/or a variation in the rate of change and particularly a slowed rate of change of the temperature at a localized area of the breast surface is an indicator of an abnormality, possibly malignant tumor or a cyst, or fibroadenoma, located in the breast at that area.

The design of the thermistor array may be a matter of choice. One design might be a series of elongate, rectangular strips with a plurality of thermistors on them. A preferred design comprises an essentially circular array of thermistors, centered on the nipple, and comprised of a plurality of circle segment panels each supporting a plurality of thermistors spaced close enough together on the respective panels and between adjacent panels as to be able to sense temperature over all localized areas of the breast.

The thermistors are seated on respective conductors on their panel. The conductors on each panel extend to a plug-in connector which can be plugged into a socket connected with a device which cycles through and senses the voltage and/or resistance of each thermistor. The sensed results are stored in a data storage, e.g., computer.

The patient is thermally stressed while measurements are taken at intervals of a few seconds apart. The change of temperature of each of the thermistors is noted, to indicate which thermistors are experiencing unusual change or unusual lack of change. The thermistor condition may be indicated by an illuminated display with illuminated areas of corresponding intensities or particular colors to indicate an anomaly or a possible hot area, or by graphs, numbers or other indicators of temperature change. The indicator should suggest localized areas for further investigation.

It is not at present intended that the apparatus or the tests described here be the final test for the presence of a malignancy. The test described may be repeated or may be supplemented or followed by any of the other standard tests, i.e., x-ray, ultrasound, or biopsy, for confirmation of a condition discovered by this test. But the apparatus and test procedure of the invention are simple, inexpensive, rapid, and effective in locating localized hot regions, or regions with differential temperature changes in order to determine normally vascularized tissue vs. neo-vascularized tissue.

Other features and advantages of the present invention will become apparent from the following description of the invention which refers to the accompanying drawings.

DESCRIPTION OF THE PREFERRED EMBODIMENTS

Figure 1:
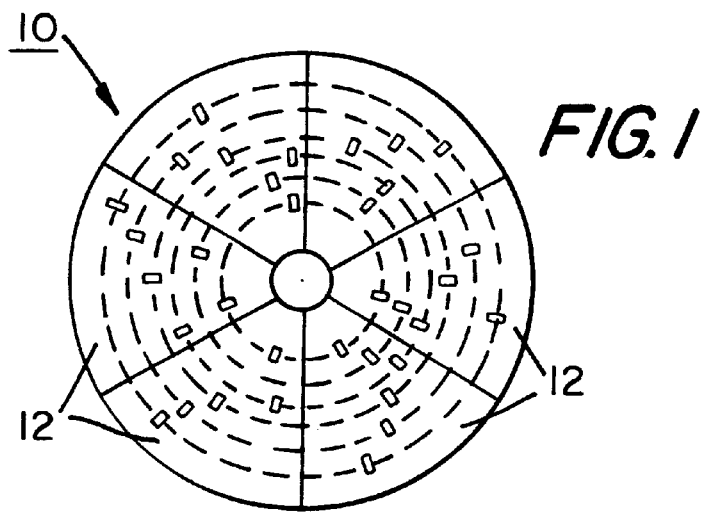
FIG. 1 is a plan view of an array of thermistors on a support according to the invention.
Figure 2:
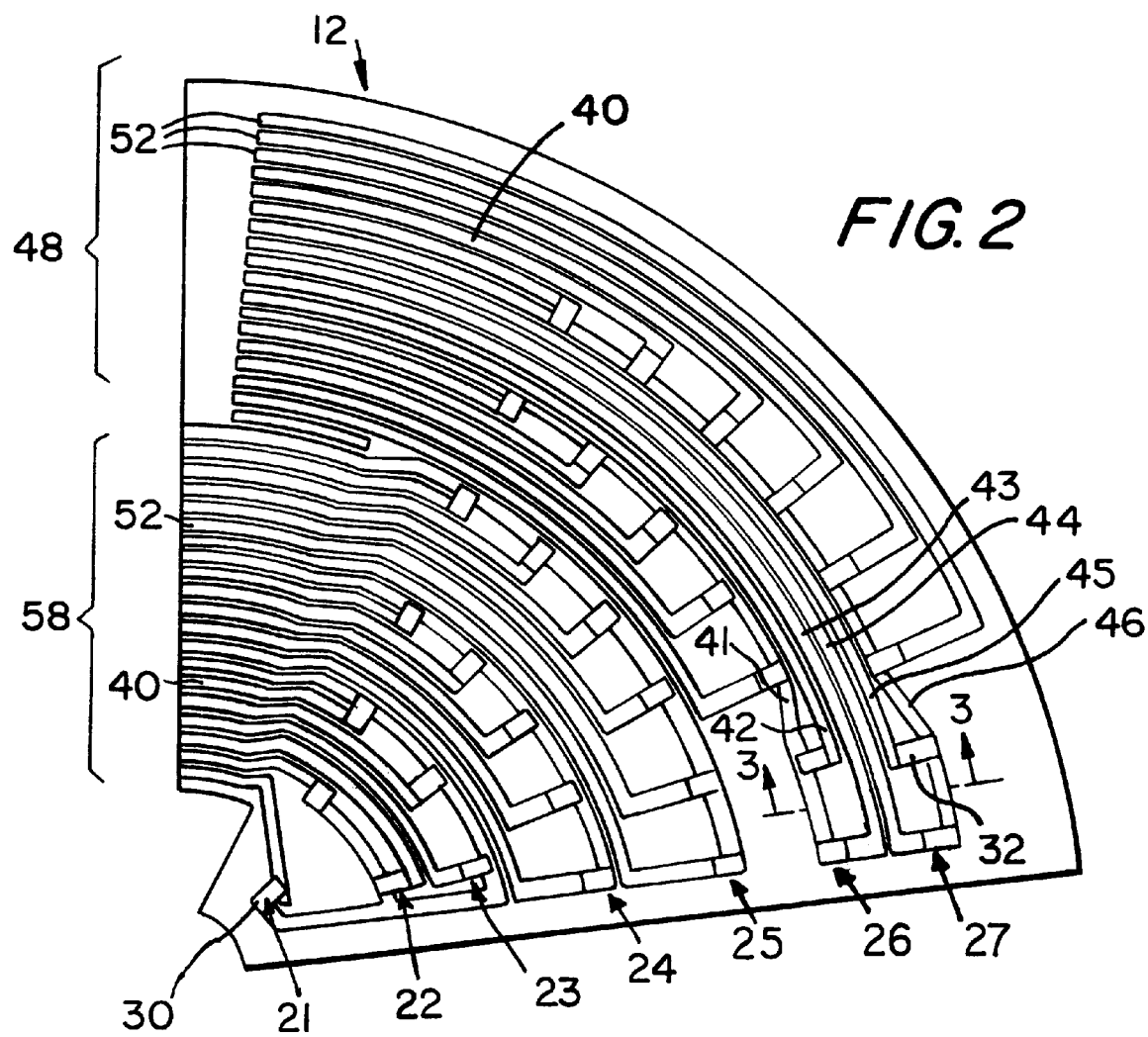
FIG. 2 is a plan view of one segment panel of the array.

The breast temperature scanner 10 of the invention, as shown in FIGS. 1 and 2, is comprised of a series of, e.g. six, individual, essentially circle segment shaped, sensor panels 12 which are adhered to the surface of the breast and preferably encircle the nipple. The panels are wrapped around, under and behind the breast for providing a full scan. The circular array of FIG. 1 gives maximum coverage over the surface of the breast. Use of several separate panels 12, rather than a single panel, allows the encircling array to be more easily conformed to the profile of the individual breast where the panels are adhered. The segment panel 12 shown in FIG. 2 is representative of all of the segments in an array 10, which would be essentially identical.

As shown in FIG. 2 and in the cross-section of FIG. 3, the sensing panel 12 includes a substrate support layer 14, which is a thin, flexible, non-stretchable sheet of a material which is hypo-allergenic and nonreactive to the skin, is heat transmissive, is capable of retaining its shape and of being conformed to the shape of the area of the breast to which it is applied and which is capable of supporting the below described conductors, etc. The substrate may be of a plastic material, e.g., one known by the trademark MYLAR, and of a thickness of 0.001 inch. The inward, skin facing surface of the substrate is coated with a thin layer 16, about 0.0025 inch thick, of a biologically inert, non-toxic, hypo-allergenic, weak, peelable adhesive, which is strong enough to adhere the panel to the skin yet permits easy peeling of the panel from the skin.

Each panel 12 and the array 10 of all the panels 12 together support several concentric rows 21–27 of temperature responsive thermistors 30. The characteristics of the thermistors are described later. As can be seen in FIG. 2, the thermistors 30 are in arrays and are so placed that they are all less than an inch apart from adjacent thermistors in both the circumferential and radial directions. Each thermistor 30 adopts the temperature to which it is exposed and therefore each detects the temperature at the breast surface in its immediate vicinity.

To support all of the thermistors, there is applied on the flexible substrate a respective pair of metal conductor strips for each thermistor. The strips are in respective concentric arrays corresponding to the respective rows 21–27 on the substrate. The conductive strips are preferably a printed circuit of about 0.001 inch thick but may also be ribbons of conductive material applied on the substrate, or may even be wires. One preferred conductor is a printed circuit of DUPONT film silver polyamide conductor. As seen in FIG. 2, like the thermistors, the conductors are in a concentric array. The conductors 41–46 are seen in FIGS. 2 and 3.

Each thermistor 30 is in a conductive path comprised of two conductors. As seen with thermistors 31 and 32 in FIGS. 2 and 3, each thermistor is supplied by a respective individual conductor 42 for thermistor 31 and 45 for thermistor 32 leading to the respective thermistor and the common ground or return conductor 41 for thermistor 31 and 46 for thermistor 32 to which all of the thermistors in the respective single arcuate row 26 and 27 of thermistors are connected. It is noted from FIG. 2 that the conductors to some of the thermistors in the rows 26 or 27 are at one radial side of the ground conductors 41 and 46 while others of the conductors to other thermistors in those rows are to the other radial side of the ground conductor 41 and 46 for the row. The same type of conductor arrangement is adapted for each of the concentric rows 21–27 of thermistors 30 on the panel 12.

All of the conductors 40, et al. extend between their respective thermistor 30 and a plug-in contact end region 52 for each conductor. Each end region is thickened and stiffened, e.g. by bending the conductor double at the end, and each end region is also bendable out of and forward of the plane of the panel 12 so as to be pluggable into a socket with respective cooperating contacts for and respective electrical circuitry for electrically connecting the thermistor for sensing its temperature sensitive voltage and/or resistance.

If needed, and as shown in FIG. 2, the conductors on the panel 12 are in a first group of conductors 48 which are radially more outward and in a second group of conductors 58 which are radially more inward. The two groups of conductors may be bent outward to varying extents or at varying locations so that the two groups of conductors may be respectively plugged into different respective sockets. This is for the mechanical convenience of the apparatus and the operator.

Figure 3:
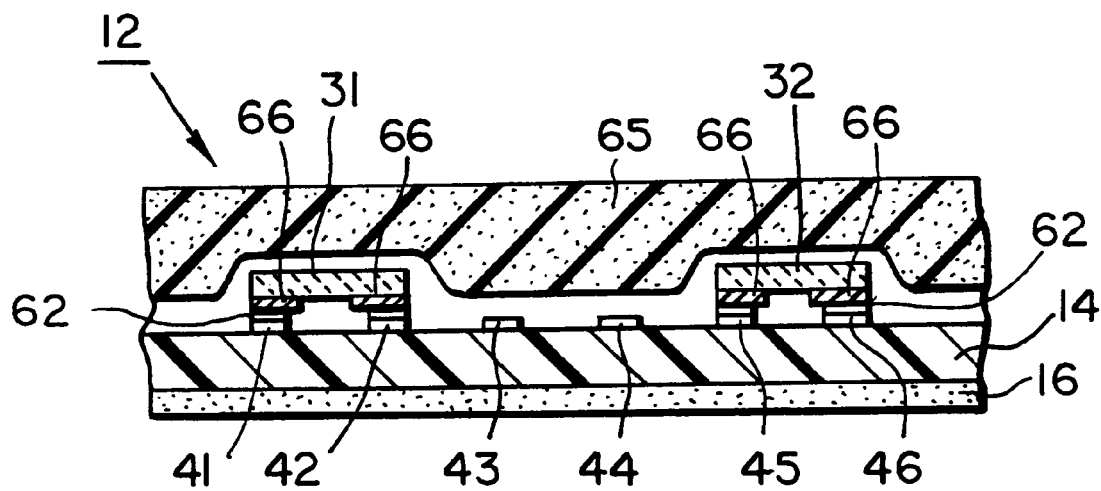
FIG. 3 is a cross-section of a fragment of the panel of FIG. 2 on the line 3—3 in FIG. 2.

As shown in FIG. 3, preferably only at the locations on the conductors where the thermistors are to be applied, supported and connected, a layer 62 of electrically conductive and adhesive epoxy is applied on the conductors to hold and electrically connect the thermistors to the conductors. That layer may be 0.00025 inch thick.

To improve accurate heat transmission from the skin to each thermistor, to retain the body heat against the thermistor and to avoid the effects of ambient temperature in the room where the sensor is used, or of a cooling or warming breeze or breath or localized wetness, etc., the outside of the panel 12 above the thermistors may be backed or covered by a flexible layer 65 of foam material which insulates and protects against the effects of the ambient environment and prevents damage to the thermistor array or its attachment caused by external contact and from applying the panel to the skin. The foam layer is also held to the thermistors, conductors and substrate 12 by an adhesive layer.

A typical thermistor 30, 31 or 32 useful here is a squared off block or chip comprised of a ceramic material, such as usually a sintered composition of cobalt, boron, manganese, or copper with silver contacts, which may be about 0.006 inch thick. Each thermistor 30, 31, 32 may have two conductive pads 66 on its surface toward the conductors, with a respective pad on the thermistor electrically connected with each of the conductors, e.g., by being adhered in place in electrical contact with the respective conductor for that thermistor by the epoxy layer 62. Other attachment techniques may be used, of course, e.g., soldering in place. Although a two pad thermistor has been described, a three pad thermistor may be used, with electric contact material also on the top surface of the thermistor that is away from the conductors to be contacted. Selection of a particular thermistor design is not a critical feature of the invention.

A thermistor is a known ceramic piece having the characteristic that its resistance varies inversely with temperature, such that the resistance decreases as the temperature increases, and vice versa, and its voltage varies with the temperature. In order for the thermistor to adjust its resistance or voltage accurately dependent upon the temperature to which it is exposed, the temperature of the entire thermistor should be uniform. To achieve this end as temperature changes, the thermistor should be of small size and small mass so that its entire body will rapidly assume the temperature to which it is exposed. As an example, a calibrated thermistor used herein may have a rated resistance of 5000 ohms at a temperature of 37° C., within a range of accuracy of ±10 ohms. Each change of 1° F. or 0.6° C. corresponds to 100 ohms, depending upon thermistor composition.

Each of the segment panels 12 in the array may be identical, or as the designer chooses, may have a smaller or greater a) number of thermistors, b) angular extent, c) number of rows of thermistors, and may be otherwise shaped than a circle segment shape. For example, a straight line, uncurved arrangement of one or more rows of thermistors on a panel is a possible arrangement with the panel being foldable, bendable, curvable, etc., as needed. What is significant here is that a large number of thermistors are supported in close enough proximity to one another as to effectively measure the localized temperatures over the entire surface of the breast.

The panel 12 is applied with the adhesive layer 16 in direct contact with the skin. The layers are thin enough and the thermistors are of such mass that the thermistors 30 stabilize at the actual skin surface temperature in a few seconds, e.g., in 2 seconds.

In order to provide adequate coverage of the surface of the breast, the array 10 and each panel 12 is of a radial size coordinated with breast size, so that different size and particularly different radius panels dependent on breast size are provided. In a typical breast scan array as shown in FIGS. 1 and 2, there may be a total of 192 thermistors, with 32 thermistors on each of six panels 12 and the thermistors are in a seven row array. There would obviously be fewer thermistors if there are fewer rows of thermistors in a particular array, e.g., 144 thermistors in a six row array useful for a smaller breast.

A complete thermistor array may include up to 192 interchangeable thermistors, which function as a network of precisely spaced reporting points on the breast surface. All thermistors are within 0.025° C. or 0.5° F. of each other and all can sense and will respond to very small temperature changes. Temperature changes can be measured during the portion of the below described test down to within 0.5° C. or 0.1° F., and such measurements for breast surface temperature have hitherto been unattainable.

Figure 4:
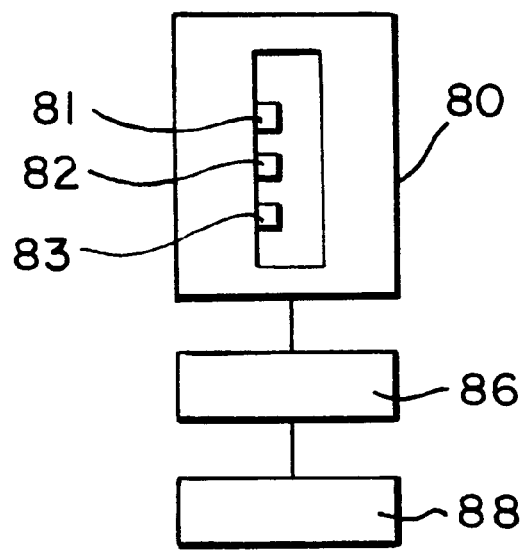
FIG. 4 schematically illustrates an information collection and storage apparatus.

After the panels 12 are applied to the skin, their connector contacts 48 and 58, etc. are plugged into a respective plug socket 80 shown in FIG. 4 in which there are respective electric contacts 81, 82, 83, et al. corresponding in position to the contacts of the conductor array. The contacts in the socket 80 are, in turn, connected via their multiple connector to a combination electronic voltage bridge and relay system 86. The bridge/relay system cycles rapidly through all of the connected thermistors and senses the voltage at each thermistor. The voltage read can be translated into a temperature reading at each thermistor. The bridge/relay system 86 is connected with a computer and data storage medium 88, wherein the temperature values that have been sensed are stored in a memory along with the exact location of each thermistor around the breast.

The relay system 86 and computer and data storage medium 88 cycles through all, for example 192, reporting points in a network in a period of perhaps 3.5 seconds and stores the readings taken, the time of each reading and the location of each thermistor in its memory.

Various temperatures will be measured over the breast surface. It is expected that the temperatures measured will not be uniform. There may be some unexpected warm or cool spots. But those alone would not be indicative of localized cysts or malignancies beneath a thermistor.

The measurements that are performed rely upon a natural process called angiogenesis which takes place in a growing cell and particularly at a cancer or malignancy. A cancer cell grows rapidly. It needs a blood supply for nutrients to grow, and a cancer cell develops its necessary blood supply. The increased blood supply also produces a localized region within the breast which is usually of higher temperature than the normal surrounding tissue. The hotter region also may elevate the skin surface temperature enabling the invention to be used.

Sometimes a cyst, which is not a malignant tumor, and which does not have an angiogenic blood supply, also is hotter than surrounding tissue due to an increased collateral blood supply around it or due to flow of blood constriction around it. The absence of angiogenesis at a nonmalignant cyst is important. Elevated localized temperature anywhere in the breast area being monitored could be interpreted as an indication of angiogenic activity. But a further test is performed with the present invention to attempt to differentiate between malignancies and non-malignant tissue or cysts.

In the process of the invention, whether or not a localized elevated surface temperature is sensed which raises suspicion of the presence there of a malignancy, the next step is to stress or "ice" the patient, in order to induce vasoconstriction, i.e., constriction of the peripheral blood vessels, including those in the breast being monitored by the invention. A patient is typically iced by using a chilled hand mitten which lowers the patient's body temperature or by applying a cold pack to the patient's feet. These areas have more Krause's receptors than any other part of the body and they transmit a signal to the autonomic nervous system to cause vasoconstriction which lowers the peripheral blood vessel system temperature and reduces the skin surface temperature. As the temperature of the surface of the breast being monitored decreases, the temperatures of all of the thermistors should decrease at a generally uniform rate. A graph of a typical drop in measured temperatures from the initial uniced reading over a period of minutes and therefore over several measurement cycles through all thermistors in an array can be generated by the computer.

In practice, it has been noted that the surface temperature readings over benign cysts, which were initially detected by the overlying skin having a higher temperature than surrounding tissue, always drop in temperature to quickly substantially match all the normal reporting points for the other thermistors during a sequence of measurements while the patient remains iced. Due to angiogenesis, malignant tumors, in contrast, lose heat more slowly and therefore often show generally little or no drop in temperature during the measuring. Once icing is completed, a short interval of exposure to normal temperature permits the patient's breast temperature to return to normal because the blood vessels return to their normal open condition.

During the temperature changing or icing portion of the test, the computer cycles through the thermistor network up to about once every five seconds. The icing results in a pattern of cooling of the normal tissue due to vasoconstriction, so that reduced temperature readings are measured during at least some of the cycle readings. Icing produces regular cooling of normal tissue, while lesions with increased metabolism, such as carcinoma, fibrocystic disease and some fibroadenomas exhibit decreased cooling patterns during the same cycling. The decreased cooling pattern in localized areas and their relationship to the cooling rate of other and normal tissue permits a diagnosis. A decreased cooling pattern versus a normal cooling pattern is measured and tested for. There are a multiplicity of reporting points to differentiate the cooling rates over the entire surface area of the breast. Cycling through the reporting points and storing results in memory every five seconds, for example, enables a readout printer or a computer screen to accurately show the location and size of any abnormality, which would be dependent upon how many and which of the thermistor temperatures are affected.

Because the above described test is noninvasive, no radiation is applied to the patient, does not use injections or dyes or anything else, the test may be repeated as often as necessary without any harm to the patient.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A temperature sensing scanner for breast temperatures, comprising:

a flexible substrate support capable of being conformed to and applied to the breast surface;

a plurality of thermistors supported on the support in an array disposed over the support so that the thermistors are spaced apart from each other so that the temperature of a localized area is sensed by an individual thermistor;

an array of conductors directly on the support at least where the thermistors are supported, at least two of the conductors connected to each of the thermistors, the conductors extending from the respective thermistors toward a connection area, the conductors being connectable with a circuit for determining at least one of the voltage and the resistance of the thermistor which is dependent upon the temperature thereof, each of the thermistors is a small block of a ceramic thermistor material having a conductor facing surface; at least a first and a second contact on the conductor facing surface and the contacts being spaced apart from each other and being respectively connectable to the respective ones of the conductors for the thermistor.

2. The arrangement of claim 1, further comprising an adhesive on the substrate support for adhering the substrate to the breast surface.

3. The arrangement of claim 2, further comprising a heat insulating layer above the thermistors, the conductors and the support layer for retaining heat at the thermistors and protecting the thermistors against localized temperature varying elements in the ambient environment.

4. The arrangement of claim 3, wherein the support is in the shape of a circle segment and the circle segment has an array of the thermistors and a respective array of the conductors thereon.

5. The arrangement of claim 1, further comprising a heat insulating layer on the outside of the support layer for retaining the heat of the body at the thermistors and protecting the thermistors against localized temperature varying elements in the ambient environment.

6. The arrangement of claim 1, wherein the thermistors on the support are arrayed in substantially concentric substantially circular rows with the thermistors within each row being spaced closely apart and the adjacent rows being spaced closely apart.

7. The arrangement of claim 6, wherein the conductors for the thermistors are in respective generally circular arcuate arrays.

8. The arrangement of claim 7, wherein each of the thermistors is connected with two of the conductors, a respective one of the conductors is a respective individual conductor for each thermistor and a respective other of the conductors is connected to a plurality of the thermistors in one of the rows as a common conductor to which the plurality of the thermistors in the row are connected.

9. The arrangement of claim 7, wherein the support for the thermistors comprises a plurality of circle segments and the segments may be applied to the breast for forming an encircling array of the thermistors; each of the circle segments having a respective circle segment array of the thermistors thereon;

a respective plurality of the thermistors of the arrangement being provided on each of the segments;

a respective set of conductors for the respective thermistors on each of the segments, and each set of the conductors extending to respective contact areas for the segment.

10. The arrangement of claim 9, wherein at least one conductor for each of the thermistors in a row thereof being radially adjacent the conductor for the next adjacent thermistor in the row.

11. The arrangement of claim 6, wherein at least one conductor for each of the thermistors in a row thereof being radially adjacent the conductor for the next adjacent thermistor in the row.

12. The arrangement of claim 1, wherein the thermistors are of such size and mass that each thermistor can adjust to the localized temperature to which it is exposed in a reasonable period of time.

13. The arrangement of claim 1, further comprising a separated connector, including contacts in the connector, each contact for contacting one of the conductors at the respective connection area;

a respective circuit connected with the contacts in the connector for each thermistor for measuring at least one of the voltage and resistance of each of the thermistors in each of the circuits;

data storage means connected with each of the circuits for storing information as to the one of the voltage and resistance of each of the thermistors, and the time at which the measurement of one of the voltage and resistance has been made at least relative to the time the measurement is made of the other thermistors.

14. The arrangement of claim 13, wherein the data storage means stores data as to the location of each thermistor on the breast.

15. A method for screening for temperature abnormalities in localized areas of the human breast, comprising:

applying an array of relatively closely spaced apart thermistors to the skin surface of the breast, spaced close together to sense the localized surface temperature of the breast over a relatively small area;

connecting each of the thermistors to an electric circuit capable of measuring at least one of the voltage and resistance of the thermistor, which is dependent upon the then current temperature of the thermistor;

during a measurement process, altering the rate of blood flow through the blood vessels of the breast for affecting measurable localized temperatures which are sensed by the thermistors, and permitting the thermistors sufficient time to change temperatures according to the change in temperature of the localized area of the breast surface to which each thermistor is applied; and measuring at least one of the voltage and resistance of each of the thermistors at spaced apart time intervals noting the differentials in the change in temperature at localized areas; and converting the voltage and resistance measurements into temperature measurements made by each of the thermistors.

16. The method of claim 15, wherein several of the measurements of the thermistors are taken at intervals of a few seconds.

17. The method of claim 15, wherein the alteration in blood flow rate in the breast is achieved by inducing vasoconstriction and measuring the rate at which the temperature at localized areas of the breast changes during vasoconstriction.

18. The method of claim 17, wherein the vasoconstriction is accomplished by icing the body of a test subject at a location remote from the breast.

19. The method of claim 15, further comprising recording the location of each of the thermistors on the breast surface so that the at least one of the measured voltage and resistance at a particular location on the breast is noted.

20. The method of claim 15, wherein the thermistors are applied in a circular array of concentric rows of closely spaced thermistors.

* * * * *